United States Patent
Faust, III

(10) Patent No.: US 7,717,292 B2
(45) Date of Patent: May 18, 2010

(54) SURGICAL INSTRUMENT CONTAINER ASSEMBLY WITH SNAP FIT HANDLE ASSEMBLY

(75) Inventor: Valentine T. Faust, III, Bow, NH (US)

(73) Assignee: Symmetry Medical, Inc., Warsaw, IN (US)

( * ) Notice: Subject to any disclaimer, the term of this patent is extended or adjusted under 35 U.S.C. 154(b) by 871 days.

(21) Appl. No.: 11/113,866

(22) Filed: Apr. 25, 2005

(65) Prior Publication Data

US 2006/0118445 A1    Jun. 8, 2006

Related U.S. Application Data

(63) Continuation-in-part of application No. 29/218,414, filed on Dec. 2, 2004, now Pat. No. Des. 560,465.

(51) Int. Cl.
B65D 25/28 (2006.01)
B65D 25/32 (2006.01)

(52) U.S. Cl. ............... 220/755; 220/752; 220/753; 16/114.1; 16/406; 16/408; 16/411; 16/421; 16/422; 16/425; 16/430; 16/434; 294/170; 294/171

(58) Field of Classification Search ......... 220/752–776; 16/114.1, 406, 408, 411, 421, 422, 425, 428, 16/430; 29/453; 294/170, 171; D8/315, D8/316
See application file for complete search history.

(56) References Cited

U.S. PATENT DOCUMENTS

| | | | | |
|---|---|---|---|---|
| 775,662 A * | 11/1904 | Lyon | ........................... | 220/755 |
| 968,440 A * | 8/1910 | Allison | ........................ | 294/168 |
| 1,020,722 A * | 3/1912 | Somerville | .................. | 294/169 |
| 1,081,559 A * | 12/1913 | Somerville | .................. | 294/169 |
| 1,501,480 A * | 7/1924 | Dye | ............................. | 16/421 |
| 1,781,583 A | 11/1930 | Hodgson | | |
| 2,102,839 A * | 12/1937 | Dohrman | ..................... | 294/171 |
| 2,319,147 A * | 5/1943 | Mason | ........................ | 220/752 |
| 2,364,105 A | 12/1944 | Socke | .......................... | 220/94 |
| 2,371,639 A * | 3/1945 | Mason | ........................ | 220/759 |
| RE22,749 E * | 4/1946 | Mason | ........................ | 220/759 |
| 2,398,436 A * | 4/1946 | Mason | ........................ | 220/752 |
| 2,488,309 A * | 11/1949 | Mason | ........................ | 220/759 |
| 2,519,186 A | 8/1950 | Herbert et al. | ................ | 16/114 |
| 2,654,115 A * | 10/1953 | Kafer | ........................... | 16/421 |
| 3,083,366 A | 3/1963 | Franges | ...................... | 16/114 |
| 3,115,229 A * | 12/1963 | Hermann | ..................... | 16/408 |
| 3,149,367 A | 9/1964 | Dills | ........................... | 16/110 |

(Continued)

FOREIGN PATENT DOCUMENTS

JP    405201453 A    8/1993

Primary Examiner—Anthony Stashick
Assistant Examiner—Ned A Walker
(74) Attorney, Agent, or Firm—Taylor & Aust, P.C.

(57) ABSTRACT

A surgical instrument container assembly includes a container and a handle assembly. The handle assembly includes at least one wire handle coupled with the container, and a pair of handle halves. Each handle half includes a pair of ends and a pair of partial openings respectively positioned at the ends. Each partial opening of one handle half is adjacent a respective partial opening of the other handle half. The adjacent partial openings conjunctively receive a portion of the at least one wire handle therein. The handle halves surround a portion of the at least one wire handle and are snap fitted together.

15 Claims, 4 Drawing Sheets

U.S. PATENT DOCUMENTS

| | | | |
|---|---|---|---|
| 3,184,101 A * | 5/1965 | Pentesco | 220/755 |
| 3,199,720 A * | 8/1965 | Sol Forman et al. | 206/162 |
| 3,912,140 A * | 10/1975 | Franges | 294/166 |
| 4,117,965 A * | 10/1978 | Rienzo | 294/167 |
| 4,207,997 A * | 6/1980 | Croyle | 294/137 |
| 4,364,150 A * | 12/1982 | Remington | 16/409 |
| 4,791,702 A * | 12/1988 | McVey | 16/428 |
| 5,088,667 A * | 2/1992 | Olson | 248/101 |
| 5,133,472 A * | 7/1992 | Koda et al. | 220/769 |
| 5,216,780 A * | 6/1993 | Lutzke et al. | 16/421 |
| 5,279,443 A * | 1/1994 | Koda et al. | 220/769 |
| 5,287,991 A * | 2/1994 | Koda et al. | 220/769 |
| 5,738,401 A | 4/1998 | Fan | 294/171 |
| D394,157 S * | 5/1998 | Dickinson et al. | D3/318 |
| 5,771,536 A * | 6/1998 | Sieg et al. | 16/431 |
| 5,931,482 A * | 8/1999 | Chirgwin | 280/33.992 |
| 6,405,409 B1 * | 6/2002 | Zirella | 16/421 |
| 6,694,666 B2 * | 2/2004 | Iwabuchi | 43/25 |
| 6,823,562 B1 * | 11/2004 | Smith et al. | 16/421 |
| 7,039,996 B2 * | 5/2006 | Crawley | 29/402.01 |
| 7,278,182 B2 * | 10/2007 | Wu | 16/113.1 |
| 2005/0006397 A1 * | 1/2005 | Borhofen | 220/755 |

* cited by examiner

SURGICAL INSTRUMENT CONTAINER ASSEMBLY WITH SNAP FIT HANDLE ASSEMBLY

CROSS REFERENCE TO RELATED APPLICATIONS

This is a continuation-in-part of U.S. Design patent application Ser. No. 29/218,414, entitled "ELLIPTICAL SNAP HANDLE ASSEMBLY", filed Dec. 2, 2004 now U.S. Pat. No. d.560,465.

BACKGROUND OF THE INVENTION

1. Field of the Invention

The present invention relates to surgical instrument cases, and, more particularly, to handle assemblies for such cases.

2. Description of the Related Art

Surgical instrument containers are known that provide organization, storage and sterilization functionality for surgical instruments and devices. Surgical procedures are regularly performed using "sets" of pre-selected surgical instruments, each set being a collection of instruments established from experience or design to be useful in a given surgical procedure. The surgical instruments expected to be used in a particular procedure are grouped together to form a set, and, as a set, are arranged in a tray or case, sterilized, and transported to the operating room for subsequent use. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances, often in a preset sequence.

To assist in transport and use, the trays and/or cases may include one or more handles which are grasped by a user. The handles may be located on the sides or top of the tray and/or case. Such handles may be in the form of, e.g., a simple wire handle allowing a user to open, move and/or transport the tray and/or case. Although such handles are functional, they tend not to be particularly ergonomic and/or easy to use.

What is needed in the art is a handle assembly for a surgical container which is easier to use, non-obtrusive, and ergonomically designed.

SUMMARY OF THE INVENTION

The present invention provides a snap fit, ergonomically designed handle assembly for a surgical instrument container.

The invention comprises, in one form thereof, a surgical instrument container assembly, including a container and a handle assembly. The handle assembly includes at least one wire handle coupled with the container, and a pair of handle halves. Each handle half includes a pair of ends and a pair of partial openings respectively positioned at the ends. Each partial opening of one handle half is adjacent a respective partial opening of the other handle half. The adjacent partial openings conjunctively receive a portion of the at least one wire handle therein. The handle halves surround a portion of the at least one wire handle and are snap fitted together.

An advantage of the present invention is that the handle halves can be snap fitted together in a quick and easy manner.

Another advantage is that the handle halves can be manufactured using a simple injection molding process and coupled together without the use of tools.

Yet another advantage is that the wire handle can be manufactured with a one piece or two piece design.

Still another advantage is that the beveled surfaces providing the snap fit can be integrally molded with one of the handle halves, or provided on a separate piece which interconnects the handle halves.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
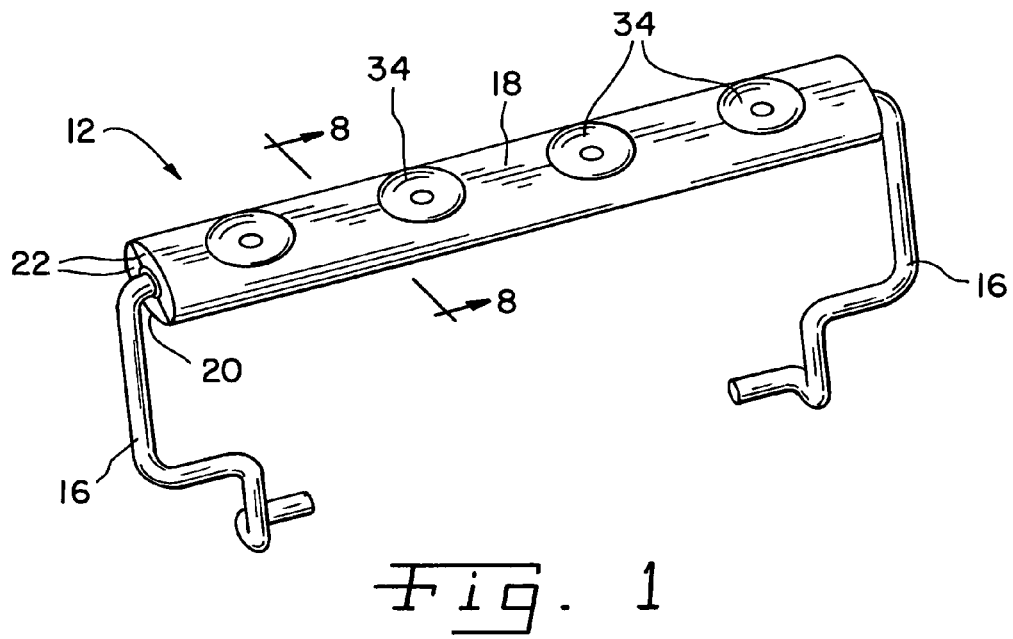
FIG. 1 is a perspective view of an embodiment of a handle assembly of the present invention used in conjunction with a surgical instrument container.
Figure 2:
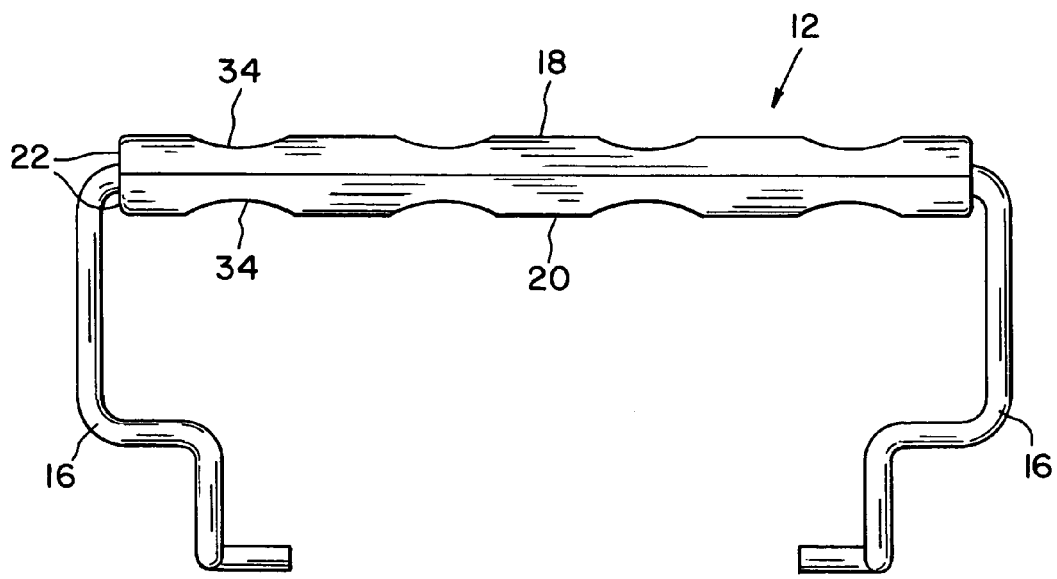
FIG. 2 is a front view of the handle assembly of FIG. 1.
Figure 3:
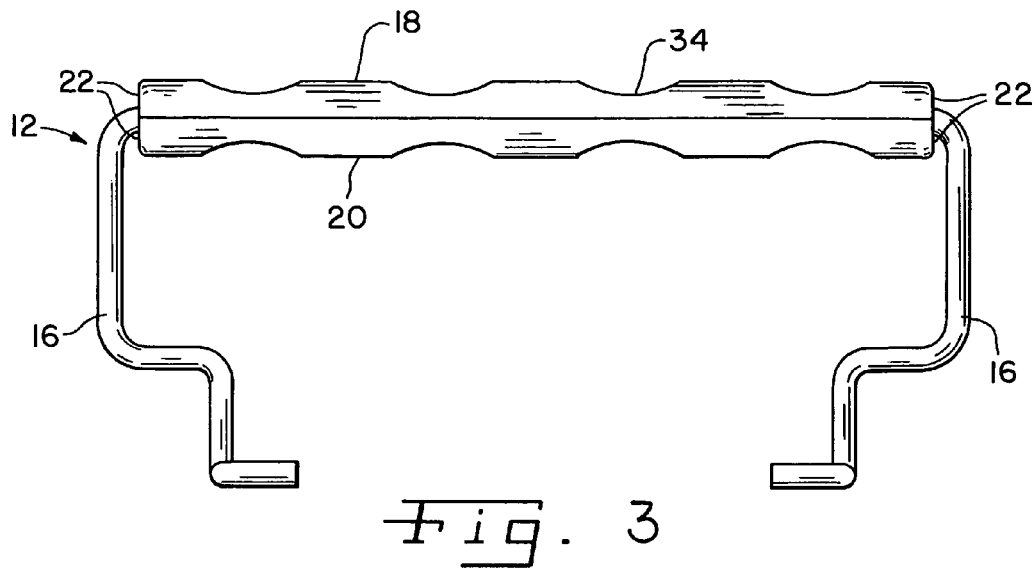
FIG. 3 is a rear view of the handle assembly shown in FIGS. 1 and 2.
Figure 4:
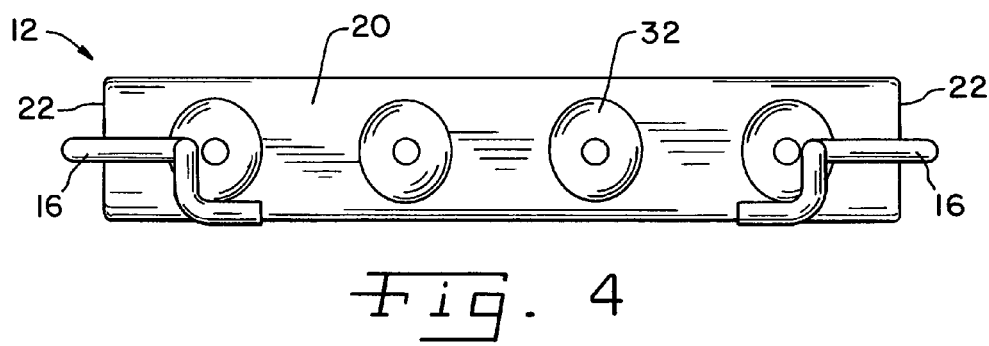
FIG. 4 is a bottom view of the handle assembly shown in FIGS. 1-3.
Figure 5:
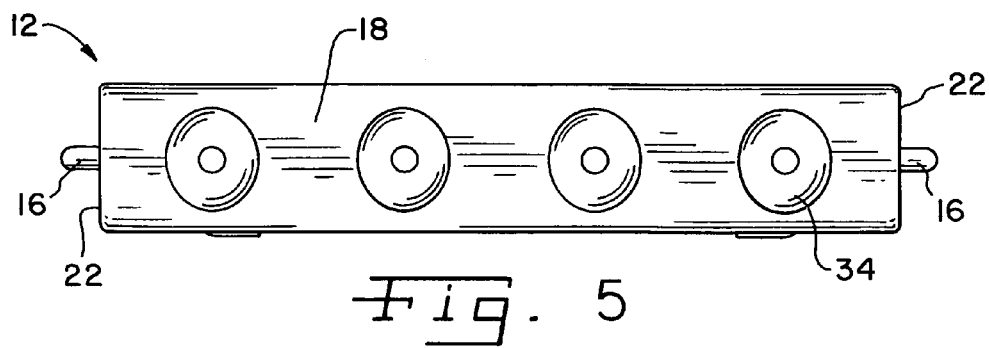
FIG. 5 is a top view of the handle assembly shown in FIGS. 1-4.
Figure 6:
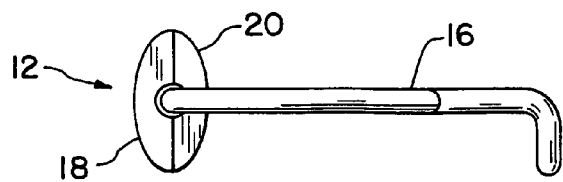
FIG. 6 is an end view of the handle assembly shown in FIGS. 1-5, the opposite end view being substantially identical.
Figure 7:
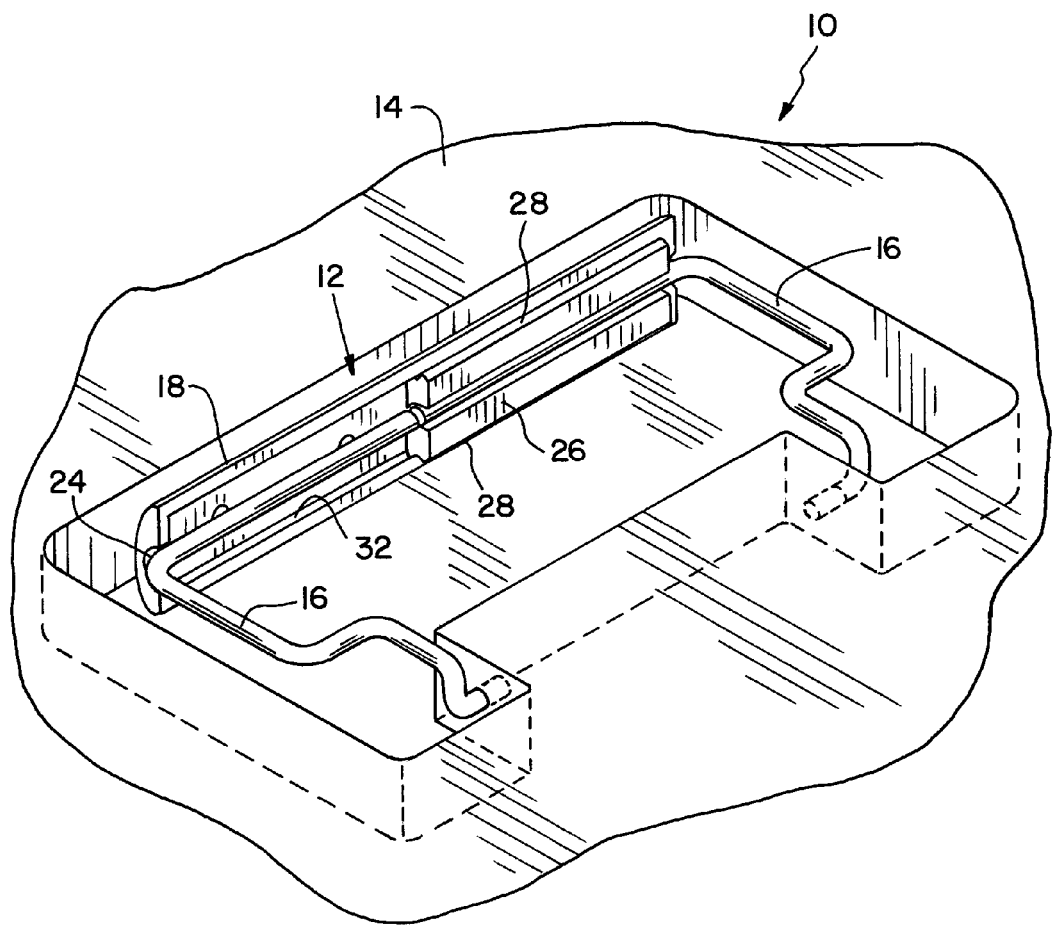
FIG. 7 is a a fragmentary, perspective view of the the handle assembly shown in FIGS. 1-6, with one of the handle halves and a portion of the snap fit block removed, pivotally coupled to a portion of a surgical instrument container.

Referring now to the drawings, there is shown an embodiment of a surgical instrument container assembly 10, which generally includes a handle assembly 12 which is attached to a container 14 (FIG. 7). Container 14 is in the form of a tray for orthopedic instruments in the embodiment shown, but may also be in the form of a drawer, case, etc.

Handle assembly 12 includes a pair of wire handles 16 pivotally coupled with container 14. Although shown as a split design, wire handle 16 may also be configured as a single wire rather than a pair of wires.

Handle assembly 12 also includes a pair of handle halves 18 and 20, which as can be seen in FIGS. 1-6 and 8 are substantially similar to each other. Handle halves 18 and 20 are also shown as being identical to each other and can be interchanged with each other. Each handle half 18 and 20 includes a pair of ends 22 and a pair of partial openings 24 respectively positioned at ends 22. Each partial opening 24 of one handle half 18 or 20 is adjacent a partial opening 24 of the other handle half 18 or 20. Each adjacent pair of partial openings 24 conjunctively receive a portion of wire handle(s) 16 therein. Handle halves 18 and 20 surround a portion of wire handle(s) 16 and are snap fitted together, as will be described in more detail hereinafter.

Figure 8:
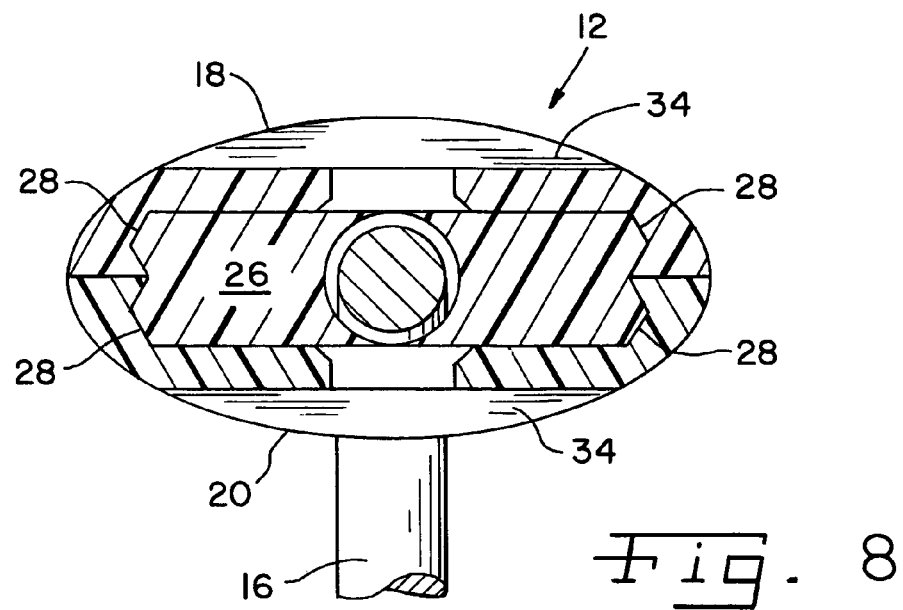
FIG. 8 is a sectional end view, taken along line 8-8 in FIG. 1.
Figure 9:
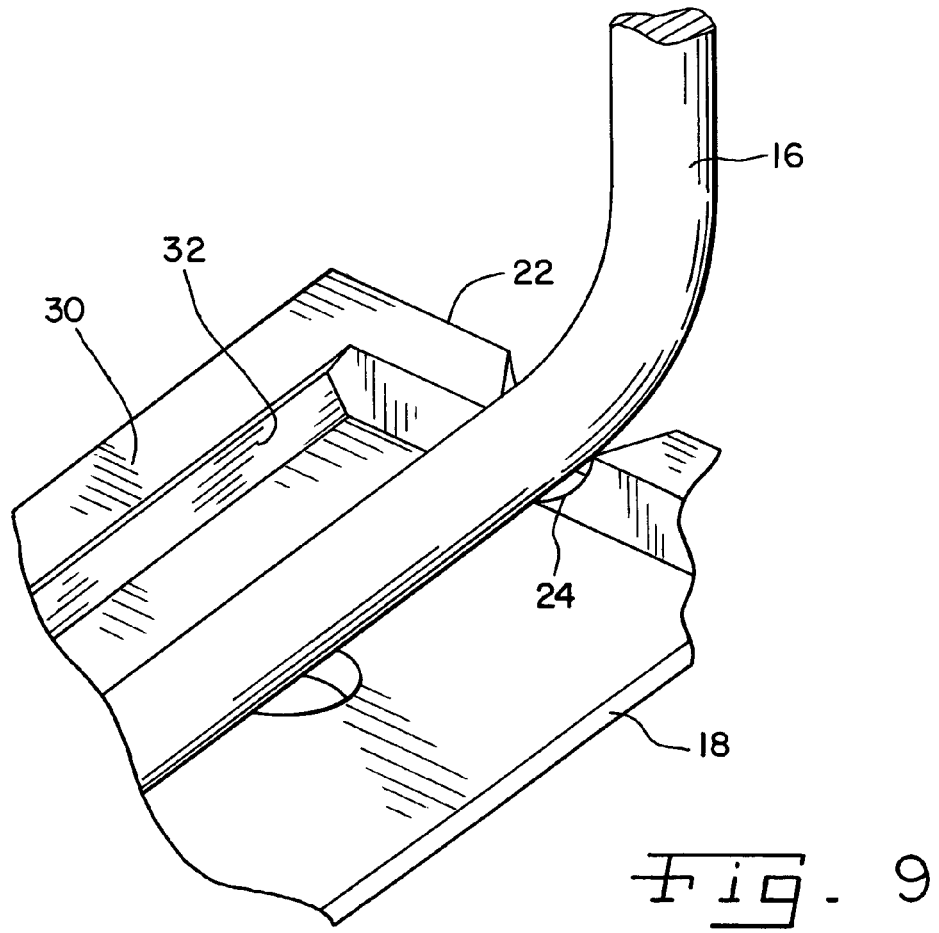
FIG. 9 is a fragmentary, perspective view of one of the handle halves, showing the recess which receives the beveled edge of the snap fit block.

Snap fit block 26 is interposed between and interconnects handle halves 18 and 20. Snap fit block 26 includes four beveled surfaces 28 extending generally parallel to each other in a longitudinal direction of handle halves 18 and 20. As can be seen in FIG. 8 snap fit block 26 is substantially symmetrical as viewed in the cross-sectional view. Each handle half 18 and 20 includes a pair of side edges 30 defining a pair of respective recesses 32 which receive a respective beveled surface 28 therein. When coupled together, beveled surfaces 28 and recesses 32 define the snap fit engagement between handle halves 18 and 20. Handle halves 18 and 20 have an elliptical cross sectional shape when snap fit coupled together.

Handle halves 18 and 20 each include a plurality of depressions 34 in an outer surface thereof. Depressions 34 provide finger depressions for the fingers of a user to further improve the ergonomic design of handle assembly 12.

Handle halves 18 and 20 and snap fit block 26 are injection molded parts in the embodiment shown. Snap fit block 26 is shown as being separate from but snap fit to each of handle halves 18 and 20. However, it is also possible to form snap fit block 26 integral with one of handle halves 18 or 20. That is, snap fit block 26 may be molded to be a monolithic part of handle half 18 or 20, and snap fit with the other handle half 18 or 20.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument container assembly, comprising:
  a container; and
  a handle assembly, including:
    at least one wire handle coupled with said container;
    a pair of handle halves, each said handle half of said pair of handle halves being identical and interchangeable, each said handle half including a pair of ends and a pair of partial openings respectively positioned at said ends, each said partial opening of one said handle half being adjacent said partial opening of an other said handle half and conjunctively receiving a portion of said at least one wire handle therein, said handle halves surrounding a portion of said at least one wire handle and being snap fitted together; and
    a snap fit block interposed between and interconnecting said handle halves, said snap fit block having a cross sectional construct that is substantially symmetrical, said snap fit block being configured for insertion into said handle halves, wherein said snap fit block includes beveled surfaces, and each said handle half includes corresponding recesses which receive said beveled surfaces.

2. The surgical instrument container assembly of claim 1, further including at least one beveled surface extending from said one handle half, said other handle half including a recess which receives said beveled surface to provide said snap fit between said handle halves.

3. The surgical instrument container assembly of claim 1, wherein said at least one wire handle comprises a pair of wire handles.

4. The surgical instrument container assembly of claim 1, wherein said at least one wire handle is pivotally attached to said container.

5. The surgical instrument container assembly of claim 1, wherein said container comprises one of a tray and a case.

6. The surgical instrument container assembly of claim 1, wherein said handle halves together have an elliptical cross sectional shape.

7. The surgical instrument container assembly of claim 1, wherein said handle halves have side edges, said snap fit block being configured to extend across said side edges.

8. The surgical instrument container assembly of claim 2, wherein each said beveled surface is one of monolithic with and separately attached to said one handle half.

9. The surgical instrument container assembly of claim 2, wherein said at least one beveled surface comprises a pair of longitudinally extending and generally parallel beveled surfaces.

10. A handle assembly for a surgical instrument container, comprising:
  at least one wire handle attachable with said container;
  a pair of handle halves, each said handle half of said pair of handle halves being identical, each said handle half including a pair of ends and a pair of partial openings respectively positioned at said ends, each said partial opening of one said handle half being adjacent said partial opening of an other said handle half and conjunctively receiving a portion of said at least one wire handle therein, said handle halves surrounding a portion of said at least one wire handle and being snap fitted together; and
  snap fit block interposed between and interconnecting said handle halves, said snap fit block having a cross sectional construct that is substantially symmetrical, said snap fit block being configured for insertion into said handle halves, wherein said snap fit block includes beveled surfaces, and each said handle half includes corresponding recesses which receive said beveled surfaces.

11. The handle assembly of claim 10, wherein said at least one wire handle comprises a pair of wire handles.

12. The handle assembly of claim 10, wherein said handle halves together have an elliptical cross sectional shape.

13. The handle assembly of claim 10, further including at least one beveled surface extending from each said handle half.

14. The handle assembly of claim 13, wherein said at least one beveled surface comprises a pair of longitudinally extending and generally parallel beveled surfaces.

15. The handle assembly of claim 13, wherein each said beveled surface is one of monolithic with and separately attached to said one handle half.

* * * * *